United States Patent
Koola et al.

(10) Patent No.: US 6,585,780 B2
(45) Date of Patent: Jul. 1, 2003

(54) CROSSLINKING AGENTS FOR TEXTILE FINISHING BATHS AND PROCESS FOR USING SAME

(75) Inventors: Johnson D. Koola, Nashville, TN (US); Lanny E. Todd, Nashville, TN (US)

(73) Assignee: Rhodia Inc., Cranbury, NJ (US)

( * ) Notice: Subject to any disclaimer, the term of this patent is extended or adjusted under 35 U.S.C. 154(b) by 183 days.

(21) Appl. No.: 09/757,995

(22) Filed: Jan. 10, 2001

(65) Prior Publication Data

US 2002/0020025 A1 Feb. 21, 2002

Related U.S. Application Data

(60) Provisional application No. 60/176,156, filed on Jan. 14, 2000.

(51) Int. Cl.$^7$ .......................... D06M 11/00; C07F 9/02; C07C 55/00
(52) U.S. Cl. .................. 8/127.1; 558/177; 558/178; 558/179; 562/590; 562/594
(58) Field of Search ........................ 8/115.51, 116.1, 8/127.1; 558/177, 178, 179; 562/590, 594

(56) References Cited

U.S. PATENT DOCUMENTS

| | | | | |
|---|---|---|---|---|
| 5,018,577 | A | 5/1991 | Pardue et al. | 166/279 |
| 5,273,549 | A | 12/1993 | Didier et al. | 8/127.1 |
| 5,300,240 | A | 4/1994 | Wilhelm et al. | 252/8.6 |
| 5,496,476 | A | 3/1996 | Tang et al. | 252/8.6 |
| 6,277,152 | B1 * | 8/2001 | Kyriazis et al. | 252/8.86 |

FOREIGN PATENT DOCUMENTS

| | | | | |
|---|---|---|---|---|
| EP | 0 454 323 A1 | 10/1991 | | C07F/9/32 |
| EP | 0 976 867 A1 | 2/2000 | | D06M/15/263 |
| WO | WO 89/12714 | 12/1989 | | D06M/13/00 |

OTHER PUBLICATIONS

International Search Report. PCT/US01/00788, filed Jan. 10, 2001.

* cited by examiner

Primary Examiner—Yogendra N. Gupta
Assistant Examiner—Preeti Kumar
(74) Attorney, Agent, or Firm—Kevin E. McVeigh

(57) ABSTRACT

Phosphinato-substituted propane- and butanepolycarboxylic acids and derivatives thereof are useful as crosslinking agents for cellulosic materials to render them wrinkle resistant and/or iron free in a durable press process.

16 Claims, No Drawings

CROSSLINKING AGENTS FOR TEXTILE FINISHING BATHS AND PROCESS FOR USING SAME

This application claims the benefit of Provisional application Ser. No. 60/176,156 filed Jan. 14, 2000.

FIELD OF THE INVENTION

This invention relates to novel crosslinking agents for use in finishing baths for textiles and to a process for finishing textiles to render the textiles wrinkle resistant and/or iron free.

BACKGROUND OF THE INVENTION

Cellulosic fabrics or textile materials are presently generally rendered wrinkle resistant or iron free in a process known as the cotton durable press process (DP process). In such a DP process, cellulosic fabrics are treated in a finishing bath with one or more finishing agents, generally to crosslink the cellulose molecules. Such crosslinking of the cellulose imparts to the fabric a tendency to return to its original shape and smoothness.

Formaldehyde, formaldehyde derivatives and formaldehyde addition products with urea, carbamate esters and other amidic compounds have been extensively used in the past as the crosslinking agents in such a process. However, serious drawbacks or problems have been found to exist with the use of such formaldehyde-derived crosslinking agents, particularly due to the release of dangerous and toxic formaldehyde vapors during the DP process and during subsequent manufacture, use, sale, laundry, and storage of garments made from such crosslinked fabric. In fact, regulations in various countries limit the dose of exposure of formaldehyde to which one can be exposed to a very low dosage amount, and for the most part effectively limit or prevent the use of such formaldehyde derivatives in the process.

In an attempt to avoid the use of formaldehyde or formaldehyde-derived crosslinking agents, several other crosslinking agents have been suggested. For example, in PCT Application No. PCT/US89102628 (WO 89/12714) of the US Department of Agriculture, there is a proposal to use organic polycarboxylic acids as crosslinking agents with hypophosphite, phosphite or polyphosphate curing catalysts to render cellulosic textile materials wrinkle free. Also, U.S. Pat. No. 5,300,240 and EP 0 976 867 A1 disclose that phosphinicosuccinic acid, phosphinicobissuccinic acid, or mixtures thereof can be used as crosslinking agents for cellulosic textile materials to render them wrinkle resistant.

However, there is still a need for other cellulosic crosslinking agents for rendering cellulosic textile materials wrinkle resistant that do not release formaldehyde vapors and yet provide wrinkle resistance to the cellulosic material that is as good as that provided by formaldehyde-derived crosslinking agents. Further, there is a need for other non-formaldehyde derived crosslinking agents that function better as cellulosic crosslinking agents than replacement crosslinking agents heretofore proposed.

SUMMARY OF THE INVENTION

It has been discovered that certain phosphinato-substituted polycarboxylic acids, and suitable salts thereof, function as superior crosslinking agents for cellulosic textile materials or fabrics. The phosphinato-substituted polycarboxylic acid cellulosic crosslinking agents of this invention are phosphinato-substituted propanetricarboxylic acids, phosphinato-substituted butanetetracarboxylic acids, oligomers thereof and mixtures thereof. Also, mixtures of the foregoing with phosphonato-substituted derivatives of these polycarboxylic acids can also be employed as crosslinking agents in a DP process for rendering cellulosic materials wrinkle resistant and iron free.

DETAILED DESCRIPTION OF THE INVENTION AND PREFERRED EMBODIMENTS

The phosphinato-substituted alkanepolycarboxylic acids and salts thereof useful for crosslinking cellulosic materials, especially in a DP process, comprise compounds of the formula (I) and obligomers thereof

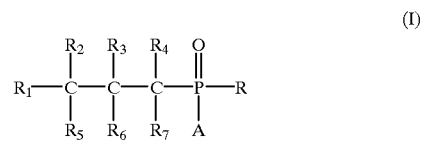

(I)

wherein R is H or

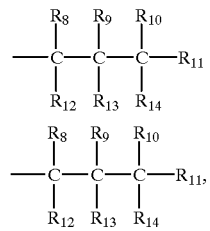

preferably

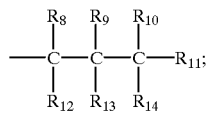

$R_1$ and $R_{11}$ are each independently H, $C_1$ to $C_4$ alkyl or —$CH_2COOM$ in which M is H, Na, K or $NH_4$, preferably $R_1$ and $R_{11}$ are H or —$CH_2COOM$ in which M is H or Na;

$R_2$, $R_3$, $R_4$, $R_8$, $R_9$ $R_{10}$ are independently H or $C_1$ $C_4$ alkyl, preferably H;

$R_5$, $R_6$, $R_7$, $R_{12}$, $R_{13}$ and $R_{14}$ are each $COOM_1$ in which $M_1$ H, Na, K, or $NH_4$, preferably —H or —Na; and A is OH, H, $C_1$ $C_8$ alkyl, cyclohexyl, aryl or $OM_2$ in which $M_2$ is H, Na, K or $NH_4$, and A is preferably OH or ONa.

A preferred class of compounds are phosphinatobis (propane-1,2,3-tricarboxylic acid) and the sodium salt thereof of formula (II) and oligomers thereof and phosphinatopropane-1,2,3-tricarboxylic acid and the sodium salt thereof of formula (III) and oligomers thereof (II)

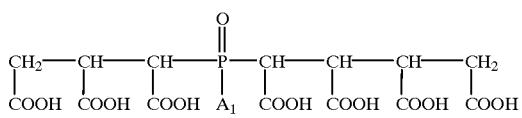

-continued

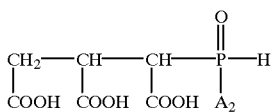
(III)

wherein $A_1$ and $A_2$ are each independently OH or ONa.

Among the oligomers of the compounds of formula (I) there may be mentioned oligomers of formula (IV)

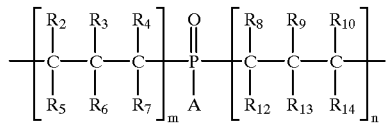
(IV)

wherein $R_2$, $R_3$, $R_4$, $R_5$, $R_6$, $R_7$, $R_8$, $R_9$, $R_{10}$, $R_{12}$, $R_{13}$, $R_{14}$ and as defined for formula (I) and m and n are each independently a small whole numeral and m plus n is greater than 2. A preferred group of oligomers are oligomers of formula (IV) in which $R_2$, $R_3$, $R_4$, $R_8$, $R_9$ and $R_{10}$ are each H; $R_5$, $R_6$, $R_7$, $R_{12}$, $R_{13}$ and $R_{14}$ are each $COOM_1$ where $M_1$ H resulting in an oligomer of formula (V)

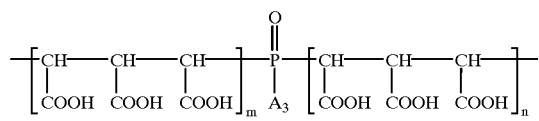
(V)

where m and n are as defined for formula (IV) and $A_3$ is OH or ONa.

Another group of oligomers of the compounds of formula (I) are oligomers of formula (VI)

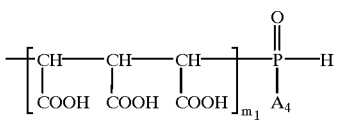
(VI)

wherein $A_4$ is OH or ONa and $m_1$ is a small whole number equal to or greater than 2.

Another crosslinking agent within the scope of formula (I) is wherein R is

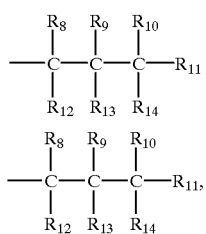

and $R_5$, $R_6$, $R_7$, $R_{12}$, $R_{13}$ and $R_{14}$ are each $COOM_1$ where $M_1$ is H; $R_1$ and $R_{11}$ are each $-CH_2COOM$ wherein M is H; $R_2$, $R_3$, $R_4$, $R_8$, $R_9$ and $R_{10}$ are each H and A is OH, namely phosphinatobis(butane-1,2,3,4-tetracarboxylic acid) or the sodium salt thereof of formula (VII),

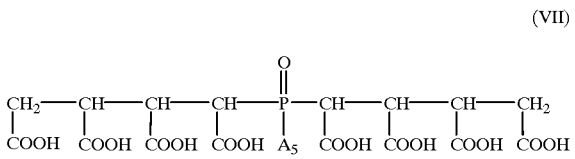
(VII)

where $A_5$ is OH or ONa.

A still further class of crosslinking agents within the scope of formula (I) are $C_1$–$C_8$ alkyl, cyclohexyl or arylbis (polycarboxyalkyl)phosphine oxides, such as butylbis(1,2,3-tricarboxypropyl)phosphine oxide of formula (VIII),

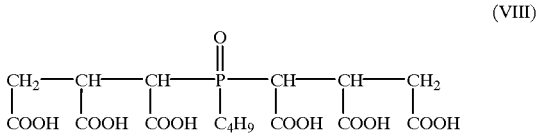
(VIII)

Compounds of formula (I) can be prepared by any suitable process, such as for example, by reacting an unsaturated acid such as prop-1-ene-1,2,3-tricarboxylic acid or but-1-ene-1,2,3,4-tetracarboxylic acid or derivatives thereof with hypophosphorous acid or an alkali metal or ammonium hypophosphite or an alkyl-, cyclohexyl-, or arylphosphine, or phosphine oxide under recognized appropriate conditions of stoichiometry, pH, temperature and free radical initiators. As examples of suitable free radical initiator, there may be mentioned persulfates such as sodium or ammonium persulfates, t-butyl hydroperoxide and other similar free radical initiators.

A process for finishing cellulosic materials, such as textiles or fabrics, is provided by employing one or more of the compounds of formula (I) and oligomers thereof and a curing catalyst in a finishing bath to treat the cellulosic material so that the cellulosic material is impregnated with the crosslinking agents of this invention. In general, the finishing bath will be a solvent solution, preferably an aqueous solution, containing a wrinkle free-providing effective amount of a crosslinking agent of this invention and a curing catalyst. Generally, the finishing bath will contain from about 2 to about 20%, preferably from about 5 to about 15% by weight of crosslinking agents, and from about 0.5 to about 10%, preferably from about 3 to about 8% by weight of curing catalyst. The finishing solution may have other suitable ingredients or agents present, such as for example, a fabric softener, solvents, wetting agents, buffers or the like. The pH of the finishing bath will generally be about pH 2 to pH 4.

In general, the cellulosic material is impregnated with the crosslinking agent and curing catalyst by immersing the cellulosic material in the finishing bath. After the cellulosic material is thoroughly wet in the finishing bath, the cellulosic material is passed between squeeze rolls to remove excess liquid. The cellulosic material is then preferably dried followed by curing in a suitable oven at a temperature of generally from about 150 to 250° C. for a period of generally up to about 15 minutes, preferably about 1 to 5 minutes, to cause crosslinking of the cellulosic material to occur. If desired, the crosslinked cellulosic material may be subsequently given a rinse to remove unreacted crosslinking agent and curing catalyst, and then redried.

The crosslinking agents of this invention can be employed to finish any suitable cellulosic material, generally any material containing about 25% or more cellulosic fibers, such as cotton, flax, jute, hemp, ramie, and regenerated unsubstituted wood cellulosic, such as rayon. The cellulosic material can be, for example, in the form of woven and nonwoven textiles, such as yarns, knit fabrics, or fibers, linters, rovings, slivers and the like.

The invention is illustrated, but not limited, by the following examples.

Preparation of crosslinking agents of this invention is illustrated by Examples 1 and 2.

EXAMPLE 1

Synthesis of Phosphinatopropane-1,2,3-tricarboxylic Acid and Oligomers 522 g (3 moles) of trans-Aconitic acid (trans-prop-1-ene-1,2,3-tricarboxylic acid) is dissolved in 500 g of water under agitation at about 70° C. To the solution is then added 300 g (2.83 moles) of sodium hypophosphite monohydrate under continuous agitation. Temperature is maintained at 70° C. A solution of 75 g (0.32 mole) of sodium persulfate dissolved in 150 g of water is introduced over a period of 7 hours into the reaction mixture kept agitated at 70° C. After the addition is complete, the reaction is allowed to continue for another 8 hours at 70° C. It is then cooled down to ambient temperature. Reaction results in 1540 g of a slightly colored clear aqueous solution. The solution contains 2.83 moles of monosodium phosphinato(propane-1,2,3-tricarboxylic acid) and its oligomers. $^{13}C$ and $^{31}P$ nmr spectra of the solution confirmed the presence of isomeric phosphinato(propane-1,2,3-tricarboxylic acid).

EXAMPLE 2

Reaction of Aconitic Acid with Sodium Hypophospite in Presence of t-Butyl Hydroperoxide 87 g (0.5 mole) of trans-Aconitic acid (trans-prop-1-ene-1,2,3-tricarboxylic acid) is dissolved in 200 g of water under agitation at about 70° C. The pH of the solution is then increased to about 7 by adding 85 g (0.69 mole) of sodium carbonate monohydrate. 25 g (0.24 mole) of sodium hypophosphite monohydrate is added to the solution while maintaining agitation. The solution temperature is then raised to about 85° C. 30 g of a 70% aqueous solution of t-butyl hydroperoxide is then introduced into the reaction mixture. The reaction is allowed to continue for another 8 hours under stirring at 85° C. The reaction mixture is then cooled down to ambient temperature. t-Butyl alcohol formed in the reaction, any unreacted t-butyl hydroperoxide and part of water are removed from the reaction mixture by distillation under reduced pressure. This process yielded a slightly colored and partially viscous solution. Analysis of the solution indicated that it is a mixture of sodium salts of isomeric phosphinato(propane-1,2,3-tricarboxylic acid), their oligomers, isomeric phosphinatobis(propane-1,2,3-tricarboxylic acid), their oligomers and isomeric phosphonatopropane-1,2,3-tricarboxylic acid.

EXAMPLE 3

When 100% cotton fabric is impregnated with the crosslinking agents of Examples 1 and 2 using sodium hypophosphite as a curing catalyst improved wrinkle resistant and iron free fabric is obtained.

A typical crosslinking experiment is completed as follows: A finishing bath is prepared by mixing the following: water 81%, crosslinking agents 8% (based on dry solids weight), ten percent aqueous solution of Tergitol™ TMN 6 1% (wetting agent), twentyfive percent aqueous solution of Mykron™ HD 2% (softening agent), twenty percent aqueous solution of Silfin™ WHP 4% (finishing agent) and sodium hypophosphite monohydrate 4% (curing catalyst).

The cellulosic material is impregnated with the finishing bath solution to a desired wet weight pickup, dried and followed by curing in a suitable oven at a temperature of 150 to 250° C. for a period of 15 minutes, preferably 1 to 5 minutes.

Control Experiment

A control experiment was carried out employing a finishing bath containing all ingredients but the crosslinking agents of examples 1 and 2.

The test swatches were washed, dried and conditioned according to the protocol $AATCC_{135}$-95.

Durable Press (DP) Rating of facbric cosslinked with the crosslinking agents of this invention was determined according to test protocol $AATCC_{124}$-96 which prduced the following results

| Fabric Crosslinking Compounds | DP Rating |
|---|---|
| Example 1 Compound | 3.3 |
| Example 2 Compound | 3.1 |
| Blank control | 2.2 |

Shrinkage of fabric crosslinked with the crosslinking agents of this invention was determined by measuring dimensional changes utilizing the test protocol of $AATCC_{135}$-95, with the following results.

| | Average dimensional change % | |
|---|---|---|
| Fabric Crosslinking Compounds | Warp | Fill |
| Example 1 Compound | −3.7 | −0.7 |
| Example 2 Compound | −4.8 | −1.0 |
| Blank Control | −9.3 | −2.2 |

Tensile strength of fabric crosslinked with the crosslinking agents of this invention was determined determined utilizing the test protocol of ASTM 5034-95, with the following results.

| | Average tensile strength (GRAB) | |
|---|---|---|
| Fabric Crosslinking Compounds | Warp | Fill |
| Example 1 Compound | 96.56 | 59.77 |
| Example 2 Compound | 98.37 | 59.72 |
| Blank Control | 141.86 | 87.61 |

Tear strength of fabric crosslinked with the crosslinking agents of this invention was determined utilizing the test protocol of ASTM 1424-96, with the following results.

| Fabric Crosslinking Compounds | Average tear strength | |
|---|---|---|
|  | Warp | Fill |
| Example 1 Compound | 3.86 | 3.56 |
| Example 2 Compound | 3.95 | 4.18 |
| Blank Control | 6.91 | 7.53 |

The whiteness index of fabric crosslinked with the crosslinking agents of this invention was measured on an Ultrascan™ XE spectrophotometer (space) from Hunter Laboratories, with the following results.

| Fabric Crosslinking Compounds | Whiteness index, % | |
|---|---|---|
|  | Before washing | After 5 washings |
| Example 1 Compound | 49.23 | 63.53 |
| Example 2 Compound | 55.79 | 65.26 |
| Blank Control | 55.90 | not available |

While the novel compounds of this invention are particularly useful as crosslinking agents for cellulosic materials, particularly for use in the cotton durable press process, they would also be useful as water-treatment chemicals, extractants for metal ions and the like.

With the foregoing description of the invention, those skilled in the art will appreciate that modifications may be made to the invention without departing from the spirit thereof. Therefore, it is not intended that the scope of the invention be limited to the specific embodiments illustrated and described.

We claim:
1. A compound of formula or oligomers thereof

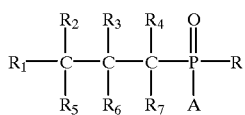

wherein R is H or

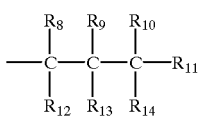

$R_1$ and $R_{11}$ are each independently H, $C_1$ to $C_4$ alkyl and —$CH_2COOM$ in which M is H, Na, K or $NH_4$;

$R_2$, $R_3$, $R_4$, $R_8$, $R_9$ and $R_{10}$ are each independently H or $C_1$ to $C_4$ alkyl;

$R_5$, $R_6$, $R_7$, $R_{12}$, $R_{13}$ and $R_{14}$ are each $COOM_1$ in which $M_1$ is H, Na, K, or $NH_4$, and A is OH, H, $C_1$ to $C_8$ alkyl, cyclohexyl, aryl or $OM_2$ in which $M_2$ is H, Na, K or $NH_4$ provided that when $R_1$ and $R_{11}$ are both present in the compound, one of $R_1$ $R_{11}$ is other than $CH_2COOM$ when A is OH.

2. A compound of claim 1 wherein A is OH; R is

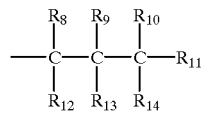

$R_1$, $R_2$, $R_3$, $R_4$, $R_8$, $R_9$, $R_{10}$ and $R_{11}$ are each H; and
$R_5$, $R_6$, $R_7$, $R_{11}$, $R_{12}$, $R_{13}$ and $R_{14}$ are each $COOM_1$ where $M_1$ is H.

3. A compound of claim 1 wherein A is OH or ONa; R, $R_1$, $R_2$, $R_3$ and $R_4$ are each H; and $R_5$, $R_6$ and $R_7$ are each $COOM_1$ where $M_1$ is H.

4. A compound of claim 1 which is an oligomer of the formula

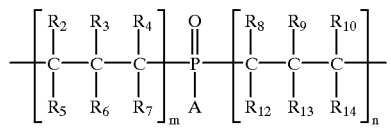

wherein $R_2$, $R_3$, $R_4$, $R_5$, $R_6$, $R_7$, $R_8$, $R_9$, $R_{10}$, $R_{12}$, $R_{13}$, $R_{14}$ and A are as in claim 1 and m and n are each independently a small whole numeral and m plus n is greater than 2.

5. A compound of claim 4 wherein $R_2$, $R_3$, $R_4$, $R_8$, $R_9$ and $R_{10}$ are each H; $R_5$, $R_6$, $R_7$, $R_{12}$, $R_{13}$ and $R_{14}$ are each $COOM_1$ where $M_1$ is H; and A is OH or Na.

6. A compound of claim 1 which is an oligomer of the formula

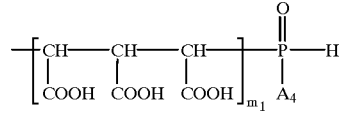

wherein $A_4$ is OH or ONa and $m_1$ is a small whole number equal to or greater than 2.

7. A compound of claim 1 wherein R is

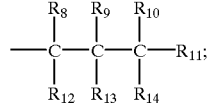

$R_5$, $R_6$, $R_7$, $R_{12}$, $R_{13}$ and $R_{14}$ are each $COOM_1$ where $M_1$ is H; $R_1$ and $R_{11}$ are each —$CH_2COOM$ where M is H, and $R_2$, $R_3$, $R_4$, $R_8$, $R_9$ and $R_{10}$ are each H and A is OH or ONa.

8. A compound of claim 1 wherein R is

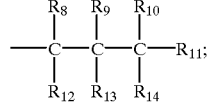

A is $C_1$–$C_8$ alkyl, cyclohexyl and aryl; $R_1$, $R_2$, $R_3$, $R_4$, $R_8$, $R_9$, $R_{10}$ and $R_{11}$ are each H; and $R_5$, $R_6$, $R_7$, $R_{12}$, $R_{13}$ and $R_{14}$ are each $COOM_1$ where $M_1$ is H.

9. A process for treating a cellulosic material to impart wrinkle resistant properties to the material, the process comprising impregnating the cellulosic material with a crosslinking agent and a curing catalyst and curing the cellulosic material, wherein the crosslinking agent comprises at least one compound or oligomer of claim 1.

10. A process for treating a cellulosic material to impart wrinkle resistant properties to the material, the process comprising impregnating the cellulosic material with a crosslinking agent and a curing catalyst and curing the cellulosic material, wherein the crosslinking agent comprises at least one compound of claim 2.

11. A process for treating a cellulosic material to impart wrinkle resistant properties to the material, the process comprising impregnating the cellulosic material with a crosslinking agent and a curing catalyst and curing the cellulosic material, wherein the crosslinking agent comprises at least one compound of claim 3.

12. A process for treating a cellulosic material to impart wrinkle resistant properties to the material, the process comprising impregnating the cellulosic material with a crosslinking agent and a curing catalyst and curing the cellulosic material, wherein the crosslinking agent comprises at least one oligomer of claim 4.

13. A process for treating a cellulosic material to impart wrinkle resistant properties to the material, the process comprising impregnating the cellulosic material with a crosslinking agent and a curing catalyst and curing the cellulosic material, wherein the crosslinking agent comprises at least one oligomer of claim 5.

14. A process for treating a cellulosic material to impart wrinkle resistant properties to the material, the process comprising impregnating the cellulosic material with a crosslinking agent and a curing catalyst and curing the cellulosic material, wherein the crosslinking agent comprises at least one compound of claim 6.

15. A process for treating a cellulosic material to impart wrinkle resistant properties to the material, the process comprising impregnating the cellulosic material with a crosslinking agent and a curing catalyst and curing the cellulosic material, wherein the crosslinking agent comprises at least one compound of claim 7.

16. A process for treating a cellulosic material to impart wrinkle resistant properties to the material, the process comprising impregnating the cellulosic material with a crosslinking agent and a curing catalyst and curing the cellulosic material, wherein the crosslinking agent comprises at least one compound of claim 8.

* * * * *